United States Patent [19]

Tsuda

[11] Patent Number: 4,983,588
[45] Date of Patent: Jan. 8, 1991

[54] MITICIDAL AGENT
[75] Inventor: Kenji Tsuda, Himeji, Japan
[73] Assignee: Diacel Chemical Industries Ltd., Sakai, Japan
[21] Appl. No.: 472,163
[22] Filed: Jan. 30, 1990
[30] Foreign Application Priority Data Feb. 1, 1989 [JP] Japan ..................................... 1-23408

[51] Int. Cl.$^5$ ............................................ A01N 55/08
[52] U.S. Cl. ..................................................... 514/64
[58] Field of Search .......................................... 514/64

[56] References Cited

PUBLICATIONS

Yamamoto et al., C. A. vol. 112, (1/15/90), 112:17755d.

*Primary Examiner*—Allen J. Robinson
*Attorney, Agent, or Firm*—Fleit, Jacobson, Cohn, Price, Holman & Stern

[57] ABSTRACT

A miticidal agent comprising alkyldimethylamine tetraborate or the hydrate thereof, for example lauryldimethylamine tetraborate, as an effective component.

1 Claim, No Drawings

MITICIDAL AGENT

BACKGROUND OF THE INVENTION

The present invention relates to a miticide which is highly safe to humans and animals.

Newly developed noncombustible building materials such as concrete, foam concrete and blocks are used for constructing buildings and houses these days; however, even with these buildings, similar to the case of conventional wooden ones, damages caused by harmful insects such as cockroaches and mites occur, which earnestly require appropriate countermeasures. In particular, damages caused by mites occur frequently: mites of many varieties as well as representative ones such as Epidermoptidae, Acaridae and Cheyletidae cause allergic rhinitis, asthma, bites or other symptoms.

Examples of miticides traditionally used against such mites include compounds known by such common names as resmethrin, phenothrin, permethrin, allethrins, tetramethrin, furamethrin, cypermethrin, decamethrin, phenvalerate, phenpropathrin, terallethrin, empenthrin and pyrethrin; pyrethroid compounds such as 1-ethynyl-2-methyl-2-pentenyl-2,2-dimethyl-3-3-(2,2-dichrolvinyl)-cyclopropane-1-carboxylate, 1-ethynyl-2-methyl-2-pentenyl-2-2-3-tetramethylcyclopropane-1-carboxylate, alpha cyano-3-phenoxybenzyl-2,2-dimethyl-3-(2,2,3-tribrometyl)-cyclopropane-1-carboxylate; organic phosphorus compounds such as Sumithion, fenthion, tetrachlorvinphos, Diazinon and DDVP; and carbamates compounds such as Baygon and Sevin.

However, the conventional miticides are highly toxic to humans and animals and not only cause rashes due to irritation to the skin but also generate environmental problems such as the contamination of water when used in large quantities.

SUMMARY OF THE INVENTION

Considering the above-mentioned conditions, an object of the present invention is therefore to provide a miticide which is not only highly effective against mites but also considerably safe to humans and animals and furthermore which can retain its pharmaceutical effect for a long period of time.

In order to achieve the above-mentioned object, the present inventor has intensively investigated and found that alkyldimethylamine tetraborate or the hydrate thereof which can be obtained by reacting alkyldimethylamine with metaborate possesses an effective miticidal activity, thereby completed the present invention.

DETAILED DESCRIPTION OF THE INVENTION

The miticide according to the present invention is characterized in that alkyldimethylamine tetraborate represented by the following general formula or the hydrate thereof is contained as an effective component.

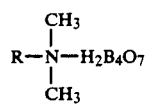

In the formula, R represents an alkyl group having 8 to 20 carbon atoms.

Alkyldimethylamine comprising the above-mentioned compound is selected from dimethylamines having an alkyl group with 8 to 20 carbon atoms, such as octyldimethylamine, decyldimethylamine, lauryldimethylamine, tetradecyldimethylamine, cetyldimethylamine and octadecyldimethylamine. The miticide of the present invention can be obtained by reacting such a dimethylamine with metaboric acid, orthoboric acid or tetraboric acid at 140° to 170° C. In this case, in an ordinary reaction, metaboric acid or orthoboric acid, particularly metaboric acid, is preferably used.

The compound obtained by the above-mentioned reaction can be used as it is as a miticide but preferably in a form of emulsion dispersed in water or in a form of solution dissolved in an organic solvent. The concentration of the above-mentioned compound as an effective component in a preparation is 0.1 to 20% by weight for practical use, and preferably 1 to 10% by weight is used.

The amount of dose of this preparation to be applied to fabric products, carpets, straw matting (tatami mats) or the like ranges between 0.1 and 10 g/m$^2$, preferably between 0.1 and 5 g/m$^2$, as the amount of effective component.

The miticide of the present invention thus exerts the miticidal effect by containing alkyldimethylamine tetraborate.

The present invention will be explained by the Examples hereinbelow in more detail, but it should be understood that the present invention is not limited to these Examples.

EXAMPLE OF PREPARATION

Lauryldimethylamine (21.3 grams, 0.1 mole) and metaboric acid (4.4 grams, 0.1 mole) were placed in a three-opening flask equipped with an evaporating device and a stirrer and reacted by heating at 140° to 150° C. for 1 hour with stirring.

About 20 minutes after the onset of the reaction, the reacting content turned to be a nearly transparent, viscous solution. Water produced during the reaction was removed outside the reaction system passing through the evaporating device. After completion of the reaction, the reaction content was cooled down to room temperature, stirred with an addition of 200 ml of hexane to extract unreacted amine and then filtered. Insoluble cakes were crushed in a powder form in a mortar; 200 ml of hexane was added again and filtration was repeated 2 times after stirring at about 50° C. for 1 hour. The resulting residue was dried in air for 1 day and then at 60° C. for 2 hours in vacuo to obtain lauryldimethylamine tetraborate. Solubility of the above-mentioned compound at different concentrations in various solvents is shown in Table 1. The solubility shown in Table 1 is at 20° C.; o represents totally soluble, Δ partly soluble, and x insoluble.

TABLE 1

| Solvent | Concentration (%) | | |
|---|---|---|---|
| | 1 | 5 | 10 |
| Water | Δ | x | x |
| Alcohol | | | |
| Isopropyl alcohol | o | o | o |
| Ethanol | o | o | o |
| Isopropyl alcohol | o | o | o |
| Ketone | | | |
| Acetone | Δ | x | x |
| Methylisobutylketone | x | x | x |
| Aromatic groups | | | |
| Benzene | o | x | x |
| Xylene | o | x | x |
| Others | | | |

TABLE 1-continued

| Solvent | Concentration (%) | | |
|---|---|---|---|
| | 1 | 5 | 10 |
| Hexane | x | x | x |
| Chloroform | o | x | x |
| Dimetylsulfoxide | o | o | x |

Subsequently, the compound obtained in Example of Preparation was tested for mutagenicity. The microorganisms used are the five strains, i.e. *Salmonella typhimurium* TA100, TA1535, TA98 and TA1537 and *Escherichia coli* wp2uvr. All of them were negative, having no mutagenicity. Furthermore, toxigenicity of the above-mentioned compound to fish were measured using cyprinodonts; the result showed the TLm value of 1.2 ppm.

TESTING EXAMPLE 1

(1) Preparation of Samples

Cloths were treated with the compound (powdered form) obtained in Example of Preparation described above at concentrations of 2.5% by weight and 5.0% by weight; a cloth without treatment was used as a control. These cloths are referred to simply as 2.5%-treated group, 5.0%-treated group and control group, respectively.

(2) Testing Procedure

The above-mentioned cloths were cut into round pieces (50 mm in diameter) and each piece was placed in the bottom of a petri dish (50 mm in inside diameter). On the surface of each piece, 200 mg of a mite medium was sprayed evenly. Nine each of the samples for the treated groups and the control group were prepared in this manner. The petri dishes thus prepared were kept under the constant temperature, at 25° C., in air-tight containers in which the humidity was controlled with a saturated salt solution.

In this case, three containers were used to keep the samples of two kinds of the treated group (i.e. the 2.5%-treated group and the 5.0% treated group) and the control group seperately. Further, the density of the mite medium was estimated by counting surviving mites 5 times in 50 mg of the medium using the saturated salt water floating method.

The samples for the two treated groups and the control group were prepared and tested for the activity against *Dermatophagoides Farinae* and *Tyrophagus putrescentiae*. Three petri dishes for individual groups were taken out weekly for the examination. Further, the examination of surviving mites in the mite medium after the test was carried out using the saturated salt solution floating method. Namely, the cloths were washed unknitting with water, the petri dishes were washed with water and then the surviving mites in the washing water were counted after washing were counted.

Tables 2 and 3 show the density of the mite medium for *Dermatophagoides farinae* and *Tyrophagus putrescentiae*, respectively.

TABLE 2

| Medium (50 mg) | 1 | 2 | 3 | 4 | 5 | Total |
|---|---|---|---|---|---|---|
| Number of surviving mite | 23 | 20 | 19 | 23 | 25 | 110 |

The estimated number of surviving mites in 200 mg: 88.0

TABLE 3

| Medium (50 mg) | 1 | 2 | 3 | 4 | 5 | Total |
|---|---|---|---|---|---|---|
| Number of surviving mites | 13 | 11 | 11 | 8 | 11 | 54 |

The estimated number of surviving mites in 200 mg: 43.2

(3) Results of the Test Against *Dermatophagoides Farinae*

Tables 4, 5 and 6 show the numbers of surviving mites (*Dermatophagoides farinae*) 5 days, 2 weeks and 4 weeks after the onset of the test, respectively.

Rates of suppression were calculated as follows:

$$1 \times \frac{\text{Number of surviving mites in the treated group}}{\text{Number of surviving mites in the control group}} \times 100 \, (\%)$$

The rates of suppression against the mites after 4 weeks (Table 6) were 97.2% for the 2.5%-treated group and 97.8% for the 5.0%-treated group.

TABLE 4

| | Petri dish # | | | |
|---|---|---|---|---|
| | 1 | 2 | 3 | Average |
| Control group | | | | |
| In the medium | 56 | 63 | 58 | |
| Cloth | 28 | 26 | 62 | |
| Petri dish | 4 | 8 | 2 | |
| Total | 88 | 97 | 122 | 102 |
| 2.5%-treated group | | | | |
| In the medium | 112 | 93 | 83 | |
| Cloth | 12 | 17 | 33 | |
| Petri dish | 4 | 2 | 1 | |
| Total | 128 | 112 | 117 | 119 |
| 5.0%-treated group | | | | |
| In the medium | 111 | 107 | 73 | |
| Cloth | 11 | 6 | 19 | |
| Petri dish | 0 | 0 | 2 | |
| Total | 122 | 113 | 94 | 110 |

Figures are the numbers of surviving mites.

TABLE 5

| | Petri dish # | | | |
|---|---|---|---|---|
| | 4 | 5 | 6 | Average |
| Control group | | | | |
| In the medium | 106 | 118 | 78 | |
| Cloth | 43 | 44 | 37 | |
| Petri dish | 4 | 6 | 7 | |
| Total | 153 | 168 | 122 | 148 |
| 2.5%-treated group | | | | |
| In the medium | 66 | 88 | 89 | |
| Cloth | 27 | 34 | 30 | |
| Petri dish | 0 | 0 | 1 | |
| Total | 93 | 122 | 120 | 112 |
| 5.0%-treated group | | | | |
| In the medium | 62 | 45 | 49 | |
| Cloth | 24 | 15 | 13 | |
| Petri dish | 1 | 0 | 2 | |
| Total | 87 | 60 | 64 | 70 |

Figures are the numbers of surviving mites.

TABLE 6

| | Petri dish # | | | |
|---|---|---|---|---|
| | 7 | 8 | 9 | Average |
| Control group | | | | |
| In the medium | 590 | 660 | 620 | |
| Cloth | 326 | 445 | 218 | |
| Petri dish | 16 | 36 | 18 | |
| Total | 932 | 1141 | 856 | 976 |

TABLE 6-continued

|  | Petri dish # | | | |
|---|---|---|---|---|
|  | 7 | 8 | 9 | Average |
| 2.5%-treated group | | | | |
| In the medium | 19 | 31 | 21 | |
| Cloth | 4 | 5 | 2 | |
| Petri dish | 0 | 0 | 0 | |
| Total | 23 | 36 | 23 | 27 |
| 5.0%-treated group | | | | |
| In the medium | 15 | 11 | 29 | |
| Cloth | 2 | 0 | 5 | |
| Petri dish | 0 | 0 | 0 | |
| Total | 17 | 11 | 34 | 21 |

Figures are the numbers of surviving mites.

(4) Results of the Test Against *Tyrophagus Putrescentiae*

Tables 7, 8 and 9 show the numbers of surviving mites (*Tyrophagus putrescentiae*) 5 days, 2 weeks and 3 weeks after the onset of the test, respectively. The rate of growth suppression against the mites after 3 weeks were 100% both for the 2.5%-treated group and the 5.0%-treated group.

TABLE 7

|  | Petri dish # | | | |
|---|---|---|---|---|
|  | 1 | 2 | 3 | Average |
| Control Group | | | | |
| In the medium | 61 | 78 | 73 | |
| Cloth | 0 | 0 | 0 | |
| Petri dish | 0 | 0 | 0 | |
| Total | 61 | 78 | 73 | 71 |
| 2.5%-treated group | | | | |
| In the medium | 22 | 28 | 47 | |
| Cloth | 0 | 0 | 0 | |
| Petri dish | 0 | 0 | 0 | |
| Total | 22 | 28 | 47 | 32 |
| 5.0%-treated group | | | | |
| In the medium | 16 | 28 | 17 | |
| Cloth | 0 | 0 | 0 | |
| Petri dish | 0 | 0 | 0 | |
| Total | 16 | 28 | 17 | 20 |

Figures are the numbers of surviving mites.

TABLE 8

|  | Petri dish # | | | |
|---|---|---|---|---|
|  | 4 | 5 | 6 | Average |
| Control group | | | | |
| In the medium | 1135 | 995 | 1329 | |
| Cloth | 4 | 2 | 12 | |
| Petri dish | 6 | 4 | 9 | |
| Total | 1145 | 1001 | 1360 | 1169 |
| 2.5%-treated group | | | | |
| In the medium | 31 | 14 | 14 | |
| Cloth | 1 | 0 | 0 | |
| Petri dish | 0 | 0 | 0 | |
| Total | 32 | 14 | 14 | 20 |
| 5.0%-treated group | | | | |
| In the medium | 1 | 0 | 2 | |
| Cloth | 0 | 0 | 0 | |
| Petri dish | 1 | 0 | 0 | |
| Total | 2 | 0 | 2 | 1 |

Figures are the numbers of surviving mites.

TABLE 9

|  | Petri dish # | | | |
|---|---|---|---|---|
|  | 7 | 8 | 9 | Average |
| Control group | | | | |
| In the medium | 3322 | 3908 | 3232 | |

TABLE 9-continued

|  | Petri dish # | | | |
|---|---|---|---|---|
|  | 7 | 8 | 9 | Average |
| Cloth | 47 | 174 | 44 | |
| Petri dish | 21 | 38 | 37 | |
| Total | 3390 | 4120 | 3313 | 3608 |
| 2.5%-treated group | | | | |
| In the medium | 0 | 0 | 0 | |
| Cloth | 0 | 0 | 0 | |
| Petri dish | 0 | 0 | 0 | |
| Total | 0 | 0 | 0 | 0 |
| 5.0%-treated group | | | | |
| In the medium | 0 | 0 | 0 | |
| Cloth | 0 | 0 | 0 | |
| Petri dish | 0 | 0 | 0 | |
| Total | 0 | 0 | 0 | 0 |

Figures are the numbers of surviving mites.

TESTING EXAMPLE 2

(1) Preparation of Samples

Filter papers were soaked with a 1% by weight water solution and a 5% by weight emulsion of the compound obtained in Example of Preparation and dried in air inside a room for 24 hours to prepare the samples.

(2) Testing Procedure

The test was carried out according to the clip method.

Namely, about 30 mites (*Dermatophagoides farinae*) were placed in the center of the filter papers (samples), and the papers were folded in two and clipped at the three corners. Then the papers were allowed to stand at 25° C.±2° C. and the life and death of the mites with the passage of time was examined under microscopy.

The results are shown in Table 10. The figures in Table 10 are the death rate of mites.

TABLE 10

| Sample | Passage of time | | |
|---|---|---|---|
|  | 24 hours | 1 week | 1 month |
| 1% solution | 93.2 | 100.0 | 100.0 |
| 5% solution | 100.0 | 100.0 | 100.0 |
| Control | 6.1 | 27.9 | 0.0 |

*Untreated filter paper. Figures are death rates (%).

It is evidently shown in Table 10 that lauryldimethylamine tetraborate exerts a marked miticidal effect against *Dermatophagoides farinae*.

EXAMPLE OF APPLICATION (1) Miticidal Sheet Laid Under Cabinet

An emulsion having the following composition was prepared (% by weight).

| Compound obtained in Example of Preparation (powdered form) | 5% |
|---|---|
| Chlorinated polypropylene* (70%) toluene solution | 11.4% |
| Toluene | 50.2% |
| Chloroethane | 33.4% |
| Total | 100.0% |

*Hardlen ®, Toyokasei Kogyo Co., Ltd.

A nonwoven fabric made of polypropylene was soaked in the suspension described above, and the soaked fabric was squeezed using a roll to remove excess fluid and dried, thereby a miticidal-treated sheet being prepared. The amount of the compound which had been obtained in Example of Preparation (powdered form) attached to the sheet was 2.2 g/m².

(2) Miticidal Sheet Laid Under Cabinet

An emulsion having the following composition was prepared (% by weight).

| | |
|---|---|
| Compound obtained in Example of Preparation (powdered form) | 5% |
| Vinyl-acetal emulsion* (50%) emulsion | 16.0% |
| Water | 79.0% |
| Total | 100.0% |

*Cevian-A 46556, Daicel Chemical Industries, Ltd.

A nonwoven fabric was soaked in the emulsion described above, and the the soaked fabric was squeezed using a roll to remove excess emulsion and dried, thereby a miticidal-treated sheet being prepared. The amount of the compound which had been obtained in Example of Preparation (powdered form) attached to the sheet was 3.7 g/m².

As demonstrated above, the miticide according to the present invention contains alkyldimethylamine tetraborate or the hydrate thereof, which possess a miticidal activity, as an effective component, exerts high safety and retain its pharmaceutical activity for a long period of time.

What is claimed is:

1. A miticidal agent, comprising an miticidal effective amount of alkyldimethylamine tetraborate having the formula

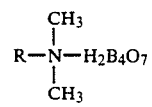

wherein R is an alkyl group having 8 to 12 carbon atoms or the hydrate thereof; and
a carrier.

* * * * *